US011699358B2

United States Patent
Monson et al.

(10) Patent No.: US 11,699,358 B2
(45) Date of Patent: Jul. 11, 2023

(54) DENTAL HYGIENE AND PERIODONTAL HAND INSTRUMENTATION TUTOR

(71) Applicant: Angela Monson, Mankato, MN (US)

(72) Inventors: Angela Monson, Mankato, MN (US); Vincent Bush, Madison Lake, MN (US)

(73) Assignee: Angela Monson, Mankato, MN (US)

( * ) Notice: Subject to any disclaimer, the term of this patent is extended or adjusted under 35 U.S.C. 154(b) by 1102 days.

(21) Appl. No.: 16/339,228

(22) PCT Filed: Oct. 3, 2017

(86) PCT No.: PCT/US2017/054934
§ 371 (c)(1),
(2) Date: Apr. 3, 2019

(87) PCT Pub. No.: WO2018/067562
PCT Pub. Date: Apr. 12, 2018

(65) Prior Publication Data
US 2019/0236980 A1 Aug. 1, 2019

Related U.S. Application Data

(60) Provisional application No. 62/403,563, filed on Oct. 3, 2016.

(51) Int. Cl.
*G09B 19/24* (2006.01)
*G09B 23/28* (2006.01)
(Continued)

(52) U.S. Cl.
CPC ............... *G09B 19/24* (2013.01); *A61B 5/00* (2013.01); *A61B 5/0077* (2013.01);
(Continued)

(58) Field of Classification Search
CPC ...... G09B 23/283; G09B 19/24; A61C 19/00; A61C 17/00; A61C 17/18; A61C 5/40; A61B 5/0088; A61B 5/0007; A61B 5/00
(Continued)

(56) References Cited

U.S. PATENT DOCUMENTS

2006/0019228 A1 1/2006 Riener et al.
2006/0024652 A1 2/2006 Ose et al.
(Continued)

FOREIGN PATENT DOCUMENTS

JP 2009-294326 A 12/2009

OTHER PUBLICATIONS

International Search Report issued in International Application No. PCT/US2017/054934, dated Jan. 24, 2018, 3 pages.

*Primary Examiner* — Kesha Frisby
(74) *Attorney, Agent, or Firm* — Hamre, Schumann, Mueller & Larson, P.C.

(57) ABSTRACT

Dental hygiene and periodontal hand instrumentation requires alignment of the cutting surface of the instrument at a specific angle and adaptation to the tooth surface. A dental hygiene and periodontal hand instrumentation tutor provides an objective, consistent and accurate way to measure and display the actual angulation and adaptation angles of a periodontal hand instrument and assess instrument use continuously. The method includes detecting the position, orientation, motion path, pressure, angulation angle, adaptation angle, and centerline angle of a periodontal hand instrument and comparing them to ideal positions, orientations, and motion paths; and provides various forms of user feedback.

8 Claims, 13 Drawing Sheets

(51) Int. Cl.
*A61C 17/00* (2006.01)
*A61B 5/00* (2006.01)
*A61C 19/04* (2006.01)
*A61C 5/40* (2017.01)
*G09B 19/00* (2006.01)
*A61C 17/18* (2006.01)
*A61C 3/00* (2006.01)

(52) U.S. Cl.
CPC .............. *A61B 5/0088* (2013.01); *A61C 5/40* (2017.02); *A61C 17/00* (2013.01); *A61C 17/18* (2019.05); *A61C 19/04* (2013.01); *G09B 19/00* (2013.01); *G09B 23/283* (2013.01); *A61C 3/00* (2013.01)

(58) Field of Classification Search
USPC ........................................................ 434/263
See application file for complete search history.

(56) References Cited

U.S. PATENT DOCUMENTS

| | | |
|---|---|---|
| 2012/0251987 A1 | 10/2012 | Huang et al. |
| 2014/0154655 A1 | 6/2014 | Bell et al. |

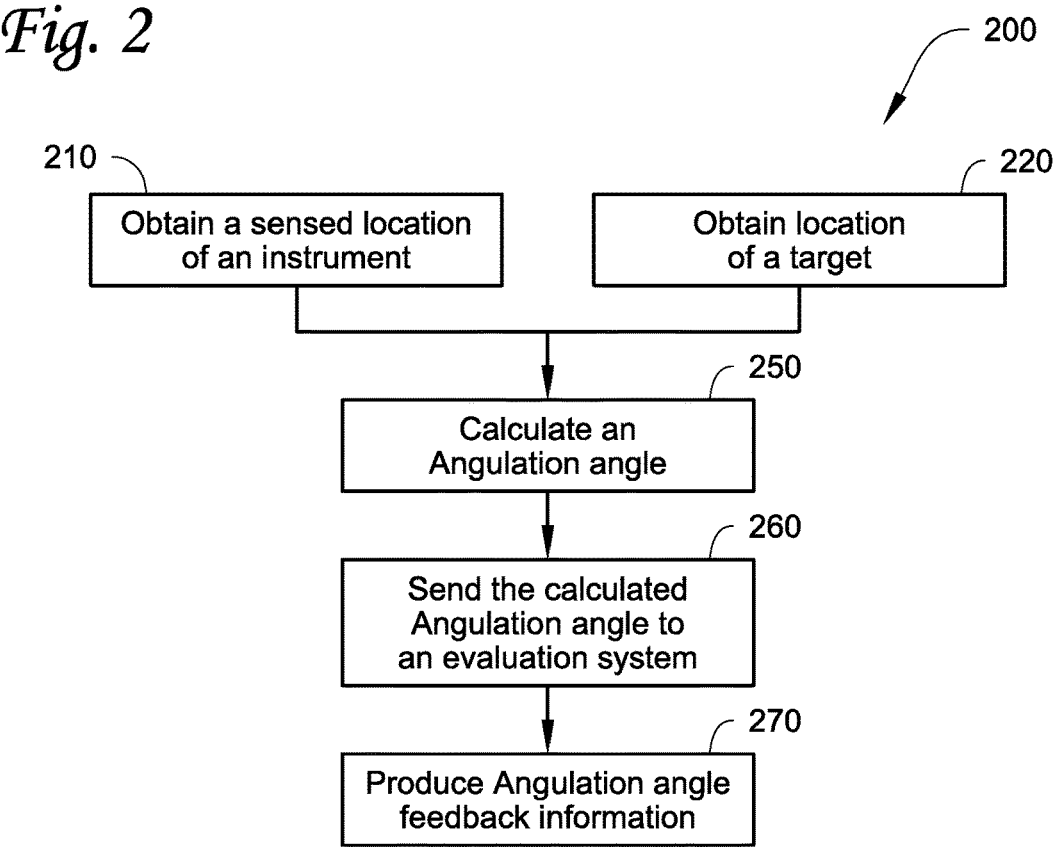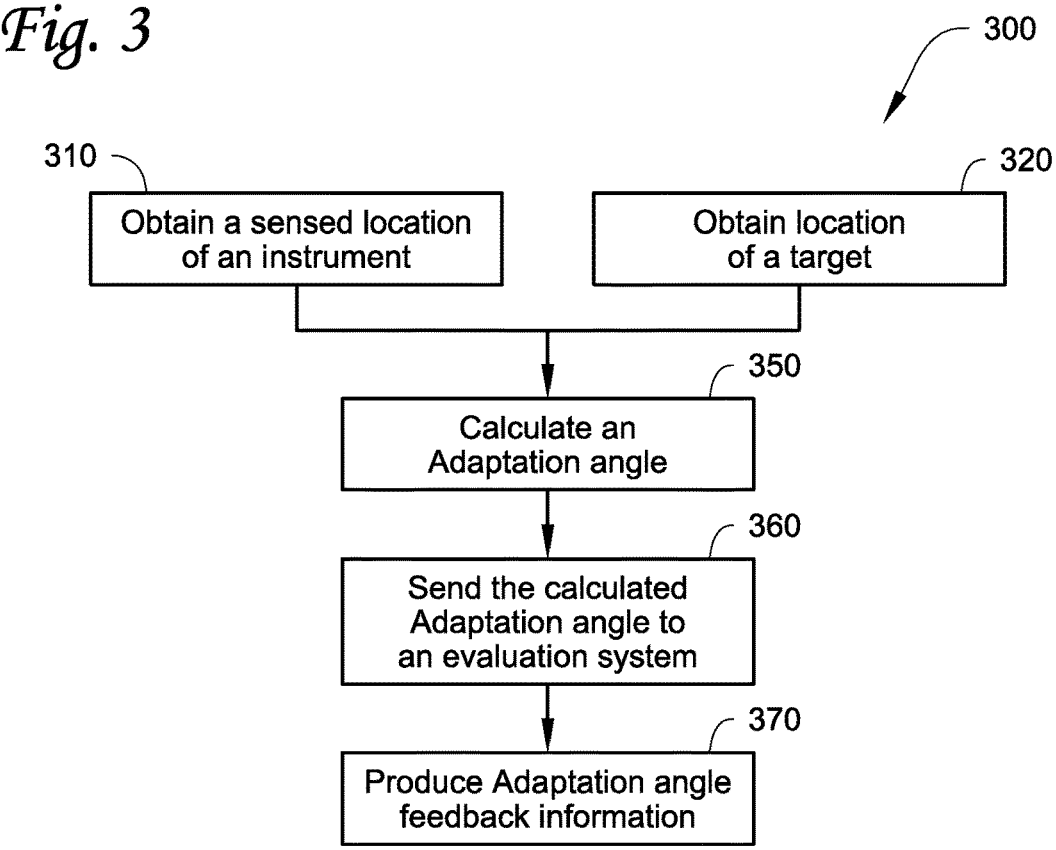

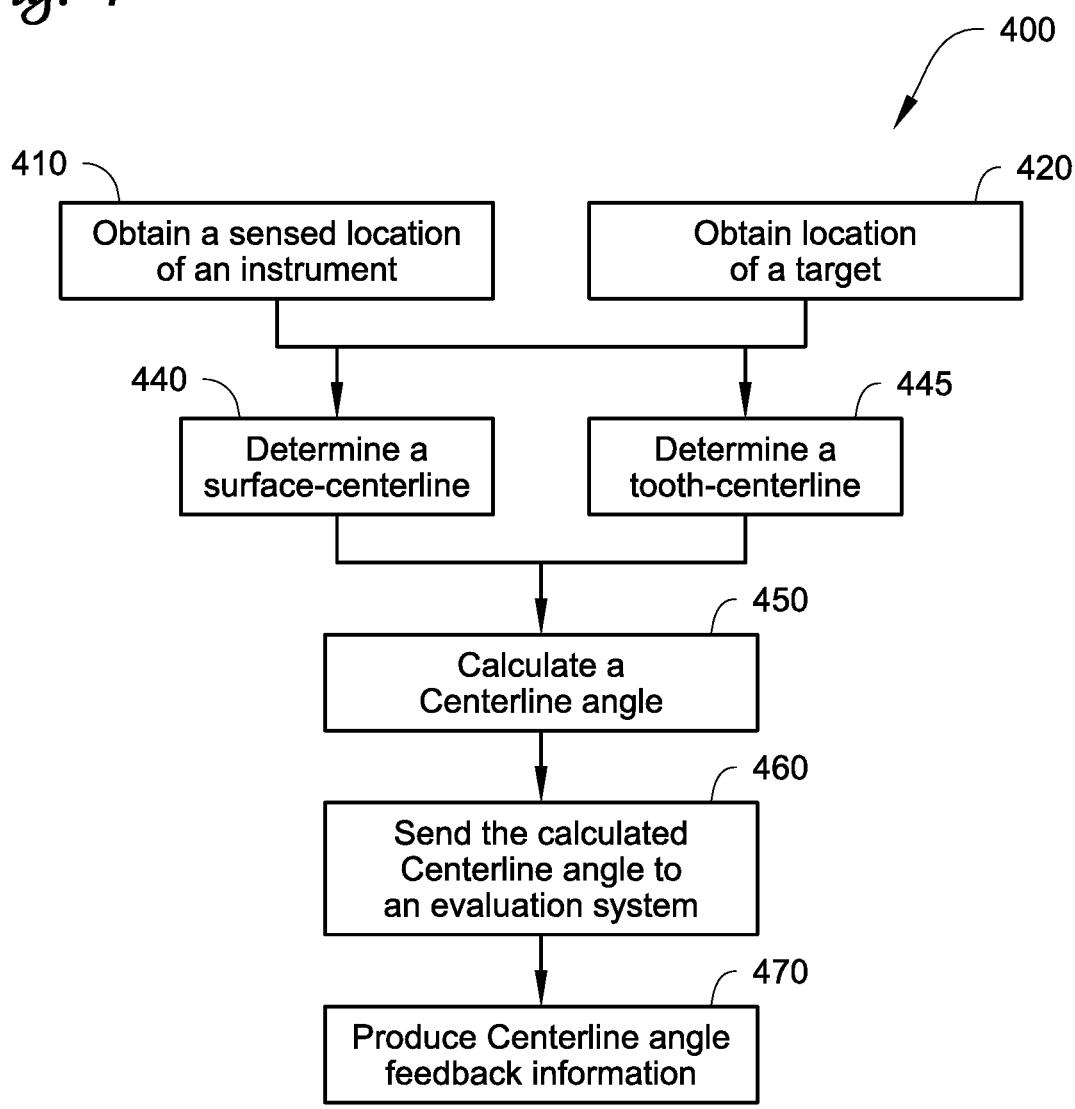

DENTAL HYGIENE AND PERIODONTAL HAND INSTRUMENTATION TUTOR

FIELD

This disclosure relates generally to dental hygiene and periodontal hand instrumentation. More specifically, the disclosure relates to a dental hygiene and/or periodontal hand instrumentation tutor and methods for operating the same.

BACKGROUND

Dental hygiene is generally taught by instructors who demonstrate a proper use of various dental hygiene and periodontal hand instrumentation (e.g., explorers, periodontal probes, scalers, etc.). Instructors then observe as students attempt to replicate the instructors' movements on a target such as a typodont. Because the instrument movements are relatively fine and visibility is limited in the confined space of the typodont, determining the correct instrument tip angles or motion paths can be difficult, or sometimes impossible, for the instructors. The instructor and/or student can only visually estimate the tip angles and other critical parameters. This visual feedback is subjective and often imprecise.

SUMMARY

A dental hygiene and/or periodontal hand instrumentation tutor and methods for operating the same are desirable to address the above problems. In some embodiments, a dental hygiene and/or periodontal hand instrumentation tutor can include an instrument sensor secured to an instrument, a tracking system communicable with the instrument sensor, a target optionally communicable with the tracking system, a core system communicable with the tracking system, a scan system communicable with the core system, and an evaluation system communicable with the core system.

In some embodiments, a target sensor can be secured to the target. In some embodiments, the target can be a typodont. A point disposed on the typodont can be located at a stored location. A location of an object includes a position (x, y, and z) and orientation (azimuth, elevation, and roll) of the object. In some embodiments, the typodont has at least one tooth that has a plurality of facets. In some embodiments, the instrument can have at least one tip that can have a cutting surface. In some embodiments, the sensor secured to the instrument can be, for example, a vibration sensor, a force sensor, an accelerometer, or the like.

In some embodiments, the tracking system can be electronically communicable with the instrument sensor. The connection between the tracking system and the instrument sensor can be wireless or through a wire. The core system can be electronically communicable with the tracking system. The connection between the core system and the tracking system can be wireless or through a wire. The scan system can be electronically communicable with the core system. The connection between the scan system and the core system can be wireless or through a wire. The evaluation system can be electronically communicable with the core system. The connection between the evaluation system and the core system can be wireless or through a wire. The sensor can be electronically communicable with the tracking system. The connection between the sensor and the tracking system can be wireless or through a wire. The target sensor can be electronically communicable with the tracking system. The connection between the target sensor and the tracking system can be wireless or through a wire.

The tracking system can vary. Suitable types of tracking systems include, but are not limited to a magnetic tracking system, a visible optical tracking system, an invisible optical tracking system, an ultrasonic tracking system, a radar tracking system, an accelerometer tracking system, a gyroscopic tracking system, an inclinometer tracking system, an inertial measurement unit tracking system, and/or a mechanical linkage tracking system.

In some embodiments, a method for operating a dental hygiene and periodontal hand instrumentation tutor can include obtaining a location of an instrument from a tracking system by a core system, the location of the instrument having an orientation and a position; obtaining a location of a target from the tracking system by the core system, the target having a surface, the location of the target having an orientation and a position; calculating an angulation angle by the core system based upon the orientation of the instrument and the orientation of the surface of the target; sending the angulation angle by the core system to an evaluation system; and producing angulation angle feedback information (such as, but not limited to, a difference between the angulation angle and at least one stored angulation angle) by the evaluation system.

In some embodiments, a method for operating a dental hygiene and periodontal hand instrumentation tutor can include calculating an adaptation angle by the core system based upon the orientation of the instrument and the orientation of the target surface; sending the adaptation angle by the core system to the evaluation system; and producing adaptation angle feedback information (such as, but not limited to, a difference between the adaptation angle and at least one stored adaptation angle) by the evaluation system.

In some embodiments, a method for operating a dental hygiene and periodontal hand instrumentation tutor can include determining a tooth-centerline by the core system based upon the location of the target; determining a surface-centerline (for example, the centerline of a cutting surface of the instrument), by the core system, based upon the location of the instrument; calculating a centerline angle by the core system based upon the surface-centerline and the tooth-centerline; sending the centerline angle, by the core system, to the evaluation system; and producing centerline angle feedback information (such as, but not limited to, a difference between the centerline angle and at least one stored centerline angle) by the evaluation system.

In some embodiments, a method for operating a dental hygiene and periodontal hand instrumentation tutor can include determining at least one tooth-facet plane/vector by the core system based upon the location of the instrument; determining a motion path of the instrument, by the core system, based on the location of the instrument and the at least one tooth-facet plane/vector; sending the location of the instrument and the motion path of the instrument by the core system to the evaluation system; and producing instrument location feedback and instrument motion path feedback information (such as, but not limited to, a difference between the location of the instrument and at least one stored instrument location, and/or a difference between the motion path of the instrument and at least one stored instrument motion path) by the evaluation system.

In some embodiments, a method for operating a dental hygiene and periodontal hand instrumentation tutor can include sensing by a tracking system a location of an instrument using an instrument sensor secured to the instrument; setting by the tracking system an output of the location of the instrument to a value defined by the location of the instrument and the stored instrument tip location; and sending by the tracking system the output of the location of the instrument to a core system.

In some embodiments, a method for operating a dental hygiene and periodontal hand instrumentation tutor can include sensing by the tracking system a location of a target using a target sensor secured to the target; setting by the tracking system an output of the location of the target to a value defined by the location of the target and the stored target location; and sending by the tracking system the output of the location of the target to the core system.

BRIEF DESCRIPTION OF THE DRAWINGS

References are made to the accompanying drawings that form a part of this disclosure and which illustrate embodiments in which the systems and methods described in this specification can be practiced.

FIG. 2 is a flowchart of a method for determining an angulation angle, according to some embodiments.

FIG. 3 is a flowchart of a method for determining an adaptation angle, according to some embodiments.

FIG. 4 is a flowchart of a method for determining a centerline angle, according to some embodiments.

Like reference numbers represent like parts throughout.

DETAILED DESCRIPTION

Figure 1:
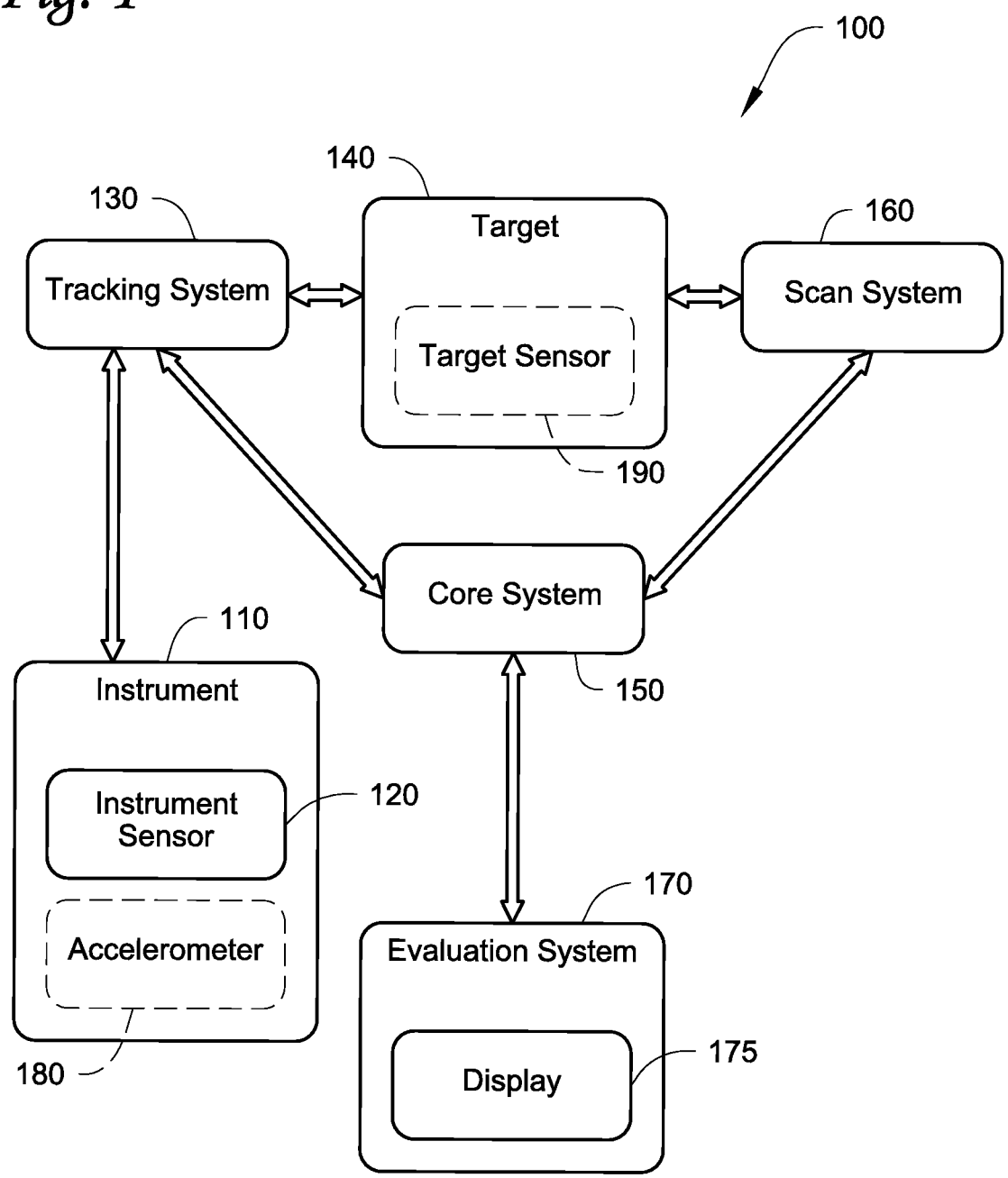
FIG. 1 is a schematic view of a dental hygiene and periodontal hand instrumentation tutor, according to some embodiments.

When teaching dental hygiene, instructors demonstrate the proper use of various dental hygiene and periodontal hand instrumentation. To assess the students, the instructors observe as the students attempt to replicate the demonstrated techniques on a target such as a typodont. The instructors are unable to measure or track tool position, orientation, or motion path. A dental hygiene and periodontal hand instrumentation tutor and methods for operating the same can eliminate subjective, inconsistent, and/or imprecise results obtained by a human observer. In some embodiment, the dental hygiene and periodontal hand instrumentation tutor and methods for operating the same can help or tutor any hygiene student, from beginner to advanced, to improve their accuracy, consistency, and/or speed when learning to use a wide variety of dental hygiene and periodontal hand instrumentation. The dental hygiene and periodontal hand instrumentation tutor and methods for operating the same can ensure the dental instrument can be used correctly to maximize the tools effectiveness and minimize the danger and/or pain to the patient.

Dental hygiene and periodontal hand instrumentation as used in this specification generally refers to an instrument which is typically used by a dental hygienist to clean a patient's teeth (e.g., above and/or below a gum line of the patient). In some embodiments, the dental hygiene and periodontal hand instrumentation can alternatively be referred to as a dental cleaning tool, periodontal hand instrumentation, dental hygiene tool, instrument, tool, or the like. The dental hygiene and periodontal hand instrumentation can have a handle and a tip. In some embodiments, the instrument tip can have a cutting surface. In some embodiments, the instrument tip does not have a cutting surface. The instrument tip can be a probe. In some embodiments, the instrument can have multiple tips (e.g., a tip at each end of the handle).

In some embodiments, a method for operating a dental hygiene and periodontal hand instrumentation tutor can include determining and tracking an actual position, orientation, and motion path of dental hygiene and periodontal hand instrumentation and using three-dimensional (3D) models of a surface of a tooth. The method for operating the dental hygiene and periodontal hand instrumentation tutor can include comparing the actual position, orientation, and motion path to ideal positions, orientations, and motion paths along one or more tooth surfaces in a target. The method for operating the dental hygiene and periodontal hand instrumentation tutor can include providing precise and consistent feedback.

In some embodiments, a method for operating a dental hygiene and periodontal hand instrumentation tutor can include measuring actual angles which include, but are not limited to, those generally referred to as angulation, adaptation, and centerline angles between an instrument tip and a tooth surface and providing continuous feedback to a user (e.g., a student) while using that instrument. It will be appreciated that the user of the dental hygiene and periodontal hand instrumentation tutor can be a user other than a dental hygiene student. For example, in some embodiments, the user may be an instructor, a dentist, a dental hygienist, a periodontist, or the like. The users are not limited to dental hygiene students.

Some advantages of embodiments of a dental hygiene and periodontal hand instrumentation tutor and methods for operating the same can include a wide variety of teaching modes and lesson plans. In some embodiments, the dental hygiene and periodontal hand instrumentation tutor and methods for operating the same can be adapted to meet specific needs of individual students. For example, students can concentrate on the techniques with which they need the most help. The dental hygiene and periodontal hand instrumentation tutor and methods for operating the same can, for example, allow students to learn at their own pace. The dental hygiene and periodontal hand instrumentation tutor and methods for operating the same can eliminate the instructor's need to monitor each student, one at a time, to ensure they are maintaining the correct instrument angles as they practice. The dental hygiene and periodontal hand instrumentation tutor and methods for operating the same can allow the instructor to manage the entire class while pinpointing the specific needs of individual students.

In some embodiments, a target can be a typodont having a point located at a stored location. FIGS. 13A-13D show a coordinate system for a transmitter and a sensor, according to some embodiments. For example, the location of the sensor is given by the position (x, y, and z) and the orientation (azimuth, elevation, and roll) as shown in FIGS. 13A-13D. In other embodiments, a target can be movable and can have a target sensor secured to the target. The target can have at least one tooth. Each tooth can have a plurality of facets.

FIG. 1 is a schematic view of a dental hygiene and periodontal hand instrumentation tutor 100, according to some embodiments. The dental hygiene and periodontal hand instrumentation tutor 100 can include an instrument 110, an instrument sensor 120 secured to the instrument 110, a tracking system 130 communicable with the instrument sensor 120, a target 140 communicable with the tracking system 130, a core system 150 communicable with the tracking system 130, a scan system 160 communicable with the core system 150, and an evaluation system 170 communicable with the core system 150. The evaluation system 170 includes a display 175. The display 175 can be, for example, a monitor, a screen, or the like.

In some embodiments, the dental hygiene and periodontal hand instrumentation tutor 100 can use magnetic tracking technology to measure a position and orientation of a tip of the instrument 110. In some embodiments, the tracking system 130 can be one of a magnetic tracking system, a visible optical tracking system, an invisible optical tracking system, an ultrasonic tracking system, a radar tracking system, an accelerometer tracking system, a gyroscopic tracking system, an inclinometer tracking system, an inertial measurement unit tracking system, and/or a mechanical linkage tracking system. In some embodiments, a suitable tracking system includes, but is not limited to, the trakSTAR™ model commercially available from Ascension Technology Corporation.

It will be appreciated that when a visible optical tracking system is used, the instrument sensor 120 can be a black and white "marker" or bull's eye that a camera tracks. The tracking system 130 can communicate with the instrument sensor (for example, the marker) via light waves (for example, optics).

In some embodiments, the tracking system 130 can include a transmitter that uses three electromagnets (coils of wire) to generate three magnetic fields in three directions (x, y and z). In some embodiments, the instrument sensor 120 can also have three coils of wire also mounted in three directions (x, y and z). In some embodiments, the instrument sensor 120 can be secured to the handle of the instrument 110. In some embodiments, the transmitter electromagnets can be turned on one at a time. A current induced in each of the three sensor coils can depend on a distance and orientation between the transmitter and the instrument sensor 120. The induced currents measured with the tracking system 130 can be used to determine the position (x, y, and z) and orientation (azimuth, elevation and roll) of the instrument sensor 120. Offsets between the instrument sensor 120 and a tip of the instrument 110 can be calibrated so the tracking system 130 outputs six degrees of freedom (6DoF) data (x, y, z, azimuth, elevation, and roll) of the tip of the instrument 110 instead of the instrument sensor 120. In some embodiments, the tracking system 130 can output (for example, analog signals, etc.) via a Universal Serial Bus (USB), a Recommended Standard—232 (RS232) serial connection, other suitable wired connection, or in some embodiments, a wireless protocol such as, but not limited to, Bluetooth, or the like, to the core system 150. In some embodiments, the core system 150 can be a specifically programmed computer running dental hygiene and periodontal hand instrumentation tutor software.

A typodont can be mounted at a fixed location with respect to the transmitter. In some embodiments, each tooth surface of the typodont can be modeled in 3D using any number of methods such as STL (STereoLithography). In some embodiments, all tooth surfaces of the typodont can be calibrated relative to the transmitter so that each facet of each tooth remains at a known and constant location and orientation relative to the transmitter. Using an output from the tracking system 130, the dental hygiene and periodontal hand instrumentation tutor 100 can measure a position of the tip of the instrument 110 and determine to which tooth facet the tip is closest. Further, when provided with the orientation of that facet and the orientation of the tip of the instrument 110, the dental hygiene and periodontal hand instrumentation tutor 100 can calculate actual angles (e.g., angulation, adaptation, and centerline angles, etc.) between the tip of the instrument 110 and the tooth surface using 3D and vector mathematics.

The evaluation system 170 can display (for example, via the display 175) user evaluation information. The user evaluation information can be in a digital, analog, graphical, avatar, alarm, and/or voice format. In some embodiments, feedback to the user can be provided in a wide variety of ways including digital or numerical values, colors, graphics (pictures, illustrations, animations, videos, and icons), sounds, vibration, voice, and suitable combinations thereof. The feedback may also include instructions (text or audible) and or 3D animations showing how to make corrections to the instrument to achieve proper instrument angles. In some embodiments, the evaluation system 170 and the core system 150 can be combined together. For example, in some embodiments, a single computer can be utilized to include the core system 150 and the evaluation system 170.

In some embodiments, a vibration sensor and/or force sensor 180 (for example, an accelerometer) can be secured to the instrument 110 and the tracking system 130 can be communicable with the vibration sensor and/or force sensor 180.

In some embodiments, a target sensor 190 can be secured to the target 140 and the tracking system 130 can be communicable with the target sensor 190.

In some embodiments, the dental hygiene and periodontal hand instrumentation tutor 100 can be used in a motion path mode. In some embodiments, angles such as, but not limited to, angulation angles, adaptation angles, and/or centerline angles, can be used to determine the motion path. The dental hygiene and periodontal hand instrumentation tutor 100 can use the tracking system 130 to record the angles (e.g., angulation angle, adaptation angle, and/or centerline angle, etc.) many times per second. The student can place the instrument 110 at point A on a tooth surface and move (for example, about 3 millimeters to about 6 millimeters) to point B.

The motion path from point A to point B can be called a "stroke." The stroke may take about 0.5 seconds (for example, for advanced students) to about 5.0 seconds (for example, for beginner students) to complete. During the stroke, the dental hygiene and periodontal hand instrumentation tutor 100 records angles (e.g., the angulation angle, the adaptation angle, and/or the centerline angle, etc.) at a rate, for example, from about 10 to about 100 times per second. During the stroke, angles (e.g., the angulation angle, the adaptation angle, and/or the centerline angle, etc.) and an amount of time to complete the stroke are important. The dental hygiene and periodontal hand instrumentation tutor 100 can have an internal timer/clock. In some embodiments, the student may use a trigger (e.g., a foot switch, a switch on the instrument 110, etc.) to indicate a beginning and end of the stroke. In some embodiments, the beginning and end of the stroke may be controlled based on, for example, placement of the instrument 110. For example, in some embodiments, the beginning of the stroke may be signaled when the student places the instrument 110 in a correct starting position (e.g., the tip of the instrument 110 is at point A) and at a correct starting orientation (e.g., correct angles such as, but not limited to, angulation angle, adaptation angle, and/or centerline angle, etc.). When the beginning is achieved, feedback information (e.g., a start signal, etc.) may notify the student to perform the stroke. In some embodiments, when the student reaches an end of the stroke (e.g., at point B) or presses the trigger to indicate the end of the stroke, the dental hygiene and periodontal hand instrumentation tutor 100 may stop recording the angles.

In some embodiments, the dental hygiene and periodontal hand instrumentation tutor 100 can use the recorded data to determine how accurately the student maintained the correct orientation (e.g., angulation angle, adaptation angle, and/or centerline angle, etc.) throughout the stroke. In some embodiments, the motion path assessment can be included in a proficiency score that the dental hygiene and periodontal hand instrumentation tutor 100 provides to the student and/or an instructor. In some embodiments, the dental hygiene and periodontal hand instrumentation tutor 100 can display the results graphically. In some embodiments, a required accuracy of the angles and time limits can be adjusted as the student becomes more proficient. In some embodiments, the type and number of stokes can be unlimited. The proficiency score from the dental hygiene and periodontal hand instrumentation tutor 100 can be more thorough, accurate, repeatable, and/or fair for the student compared to using human observers.

Figure 5:
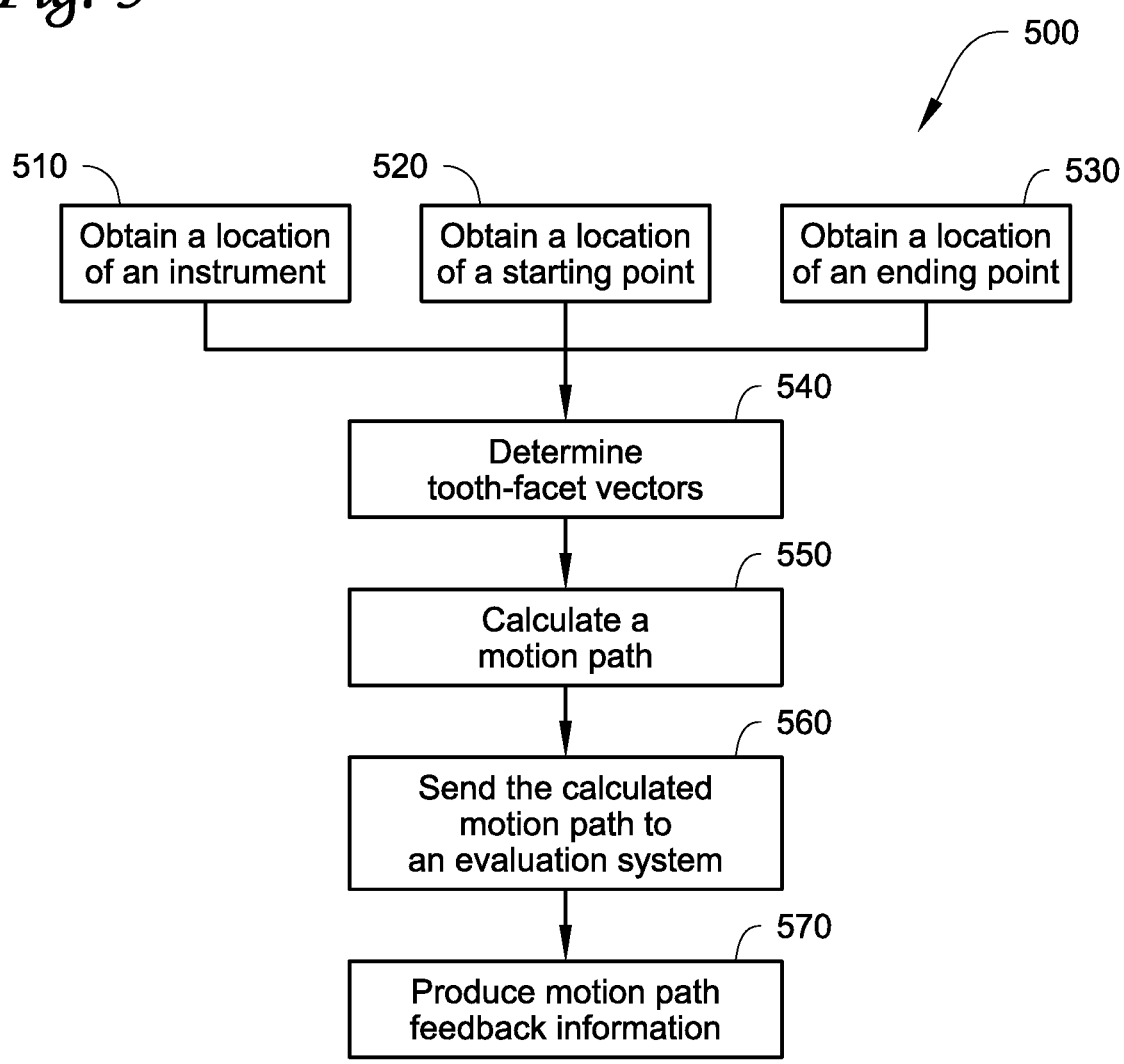
FIG. 5 is a flowchart of a method for determining an instrument location and motion path, according to some embodiments.

FIG. 2 is a flowchart of a method 200 for determining an angulation angle, according to some embodiments. FIG. 3 is a flowchart of a method 300 for determining an adaptation angle, according to some embodiments. FIG. 4 is a flowchart of a method 400 for measuring a centerline angle, according to some embodiments. FIG. 5 is a flowchart of a method 500 for determining an instrument location and motion path, according to some embodiments.

A location of an instrument (e.g., the instrument 110 in FIG. 1) is obtained by a core system (e.g., the core system 150 in FIG. 1) from a tracking system (e.g., the tracking system 130 in FIGS. 1) at 210, 310, 410, and 510. The location of the instrument 110 includes an orientation and a position. The location of the instrument 110 can be tracked/sensed by the tracking system 130. In some embodiments, the location (as sensed) can be referred to as the sensed location, the tracked location, the determined location, or the like. At 220, 320, and 420 a location of a target (including tooth-facets of the target 140 in FIG. 1) is obtained by the core system 150 from the tracking system 130. The target 140 can have at least one tooth, and each tooth can have a plurality of facets. Each facet has an internal/relative facet location and a facet normal unit vector. In some embodiments, the normal unit vector can be included, or part of, data stored in a file (for example, an STL file) for each facet of a target. In addition, the normal unit vector can be calculated from the three vertices (for example, 1, 2, 3 in FIG. 11C) that are also included, or part of, the data stored in the STL file.

At 440, a surface-centerline (for example, a centerline of a cutting surface of the instrument 110) is determined, by the core system 150, based upon the location of the instrument 110. At 540, a tooth-facet vector is determined, by the core system 150, based upon the location of the target surface and the location of the instrument 110. In some embodiments, the core system 150 identifies a facet that is closest to the location of the instrument 110 based on the location of the target surface. When the instrument 110 is moved to a different location, another tooth-facet is identified. Once the facet is identified, the tooth-facet vector, which is the normal unit vector (N) of that facet, can be determined. The tooth-centerline can be determined as well. FIG. 11c shows the normal unit vector of one facet of a tooth, according to some embodiments. In FIG. 4, at 445 a tooth-centerline is determined by the core system 150, based upon the location of the target surface and the location of the instrument 110.

Figure 15:
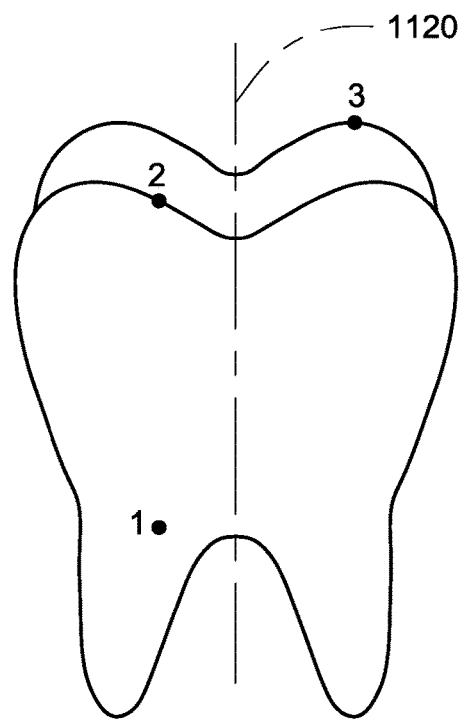
FIG. 15 shows calibration spots on a target for target calibration, according to some embodiments.

In some embodiments, each target (for example, a tooth) can have a specified centerline and the centerline information does not need to be stored in a separate configuration file. In some embodiments, the centerline information can be obtained from the STL data of that target using the following technique. As shown in FIG. 15, target calibration uses at least three calibration spots on the target in order to compensate for both position (x, y, and z) and orientation (azimuth, elevation, and roll) of the target with respect to the transmitter. The first two calibration spots can be chosen so a vector calculated between spot number 1 and number 2 will be parallel with and in the same direction as the centerline of that target. This can eliminate having a separate centerline calibration data or a file. The centerline vector is used to calculate the centerline angle and can also be used to point toward the occlusal surface of the target so the system can determine the root and crown ends of a target tooth for both upper and lower jaw teeth.

In some embodiments, each calibration spot (shown in FIG. 15) is a vertex of a facet listed in the STL file for that target tooth. Those vertices can be selected and identified so the system can compute a vector from calibration spot (vertex) 1 to calibration spot (vertex) 2 and that vector will be substantially parallel to the centerline.

Returning to FIGS. 2-5, in some embodiments, 520 and 530 respectively obtain a location of a starting point (point A) and an ending point (point B). In some embodiments, obtaining a starting point and/or an ending point may use a foot switch or may be semiautomatic.

In some embodiments, 250, 350, 450, and 550 respectively calculate an angulation angle, an adaptation angle, a centerline angle, or a motion path, by the core system, based upon the orientation of the instrument, the tooth-facet vector, the orientation of the target surface, the tooth-centerline, the surface-centerline, and/or the starting and/or ending point of a motion path.

At 260, 360, 460, and 560, the calculated angulation angle, adaptation angle, centerline angle, or the motion path, is sent by the core system 150, to an evaluation system (e.g., the evaluation system 170 in FIGS. 1). At 270, 370, 470, and 570, angulation angle, adaptation angle, centerline angle, or motion path feedback information (such as, but not limited to, a difference between the angulation angle, adaptation angle, centerline angle, or motion path and a stored angulation angle, adaptation angle, centerline angle, or motion path) is produced by the evaluation system 170. In some embodiments, the feedback information can help eliminate subjective, inconsistent, and/or imprecise results obtained by a human observer; can help or tutor any hygiene student, from beginner to advanced, to improve their accuracy, consistency and speed when learning to use a wide variety of dental hygiene and periodontal hand instrumentation; and can ensure the dental instrument is used correctly to maximize the tools effectiveness while minimizing the chance of harm to a live patient.

In some embodiments, the evaluation system 170 can display one or more of the determined angulation angle, the at least one stored angulation angle, the determined adaptation angle, the at least one stored adaptation angle, the determined centerline angle, the at least one stored centerline angle, the location of the instrument, the at least one stored instrument location, the determined motion path of the instrument, the calculus detection, and/or the at least one stored instrument motion path.

In some embodiments, the evaluation system 170 can display a dental hygiene proficiency score and/or a dental hygiene scaling score. Methods for operating the dental hygiene and periodontal hand instrumentation tutor 100 can include tracking the progress of each student and their abilities and reporting those finding to an instructor, and/or creating future lesson plans for individual students based on their individual needs and their past scores.

In some embodiments, the system (for example, the evaluation system 170 or the core system 150) can compute a proficiency score based on one or more of the following but not limited to the following parameters: (1) how well the angulation angle is maintained throughout the entire stroke, (2) how well the adaptation angle is maintained throughout the entire stroke, (3) how well the centerline angle is maintained throughout the entire stroke, (4) accuracy of the starting point of a stroke, (5) accuracy of the ending point of a stroke, (6) how well the instrument motion path tracks the ideal motion path, (7) how much time it takes to complete that motion, (8) which instrument is used and which end of the instrument is used, (9) how much lateral force is applied to the cutting edge, (10) how much calculus was discovered or missed, (11) how well one or more quadrant of teeth were cleaned, (12) "thoroughness" of the student by, for example, displaying the areas of the tooth that were not touched by the instrument, etc.

In some embodiments, the system (for example, the evaluation system 170 or the core system 150) can optimize the computation of the proficiency score for different teaching institutions or different skill levels by making selections that determine, for example, (1) which of many parameters will be used to generate the score, and/or (2) the priority and weight assigned to each of the parameters selected. The optimization can include password protection to prevent unauthorized changes.

In some embodiments, the system (for example, the evaluation system 170 or the core system 150) can provide a list of possible proficiency scores that are previously defined, named, and stored for future use to make it quick and easy to reuse a particular proficiency score.

In some embodiments, tip calibration can be eliminated by using assembly of the tracking sensor into the instrument handle that provides proper positioning and orientation of the sensor relative to the tip and cutting surface of the instrument. In some embodiments, a method of calibrating the location (position and orientation) of the sensor after the sensor is mounted is disclosed so the tracking system outputs the position of the instrument tip and outputs the orientation of the cutting surface as if the sensor is replaced by the instrument tip as shown by the dotted arrow in FIG. 13.

Figure 6:
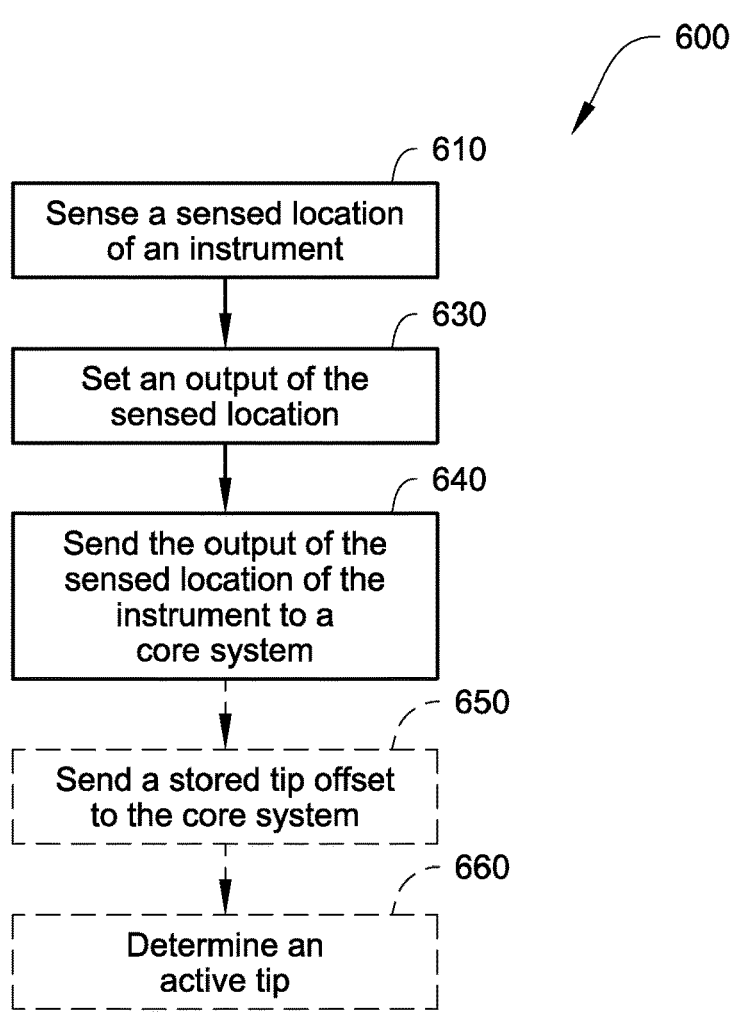
FIG. 6 is a flowchart of a method for calibrating an instrument, according to some embodiments.

FIG. 6 is a flowchart of a method 600 for calibrating an instrument (e.g., the instrument 110 in FIG. 1), according to some embodiments. The method 600 includes 610 sensing, by a tracking system (e.g., the tracking system 130 in FIG. 1), a location of the instrument 110 using an instrument sensor (e.g., the instrument sensor 120 in FIG. 1) secured to the instrument 110.

At 630 the tracking system sets an output of the location of the instrument 110 to a value defined by the location of the instrument 110 and the stored instrument tip location. This step shifts the output of the location of the instrument 110, by the tracking system 130, to the instrument tip location instead of the instrument sensor (that is secured on the instrument) location as if the instrument tip is replaced by the sensor as shown by the dotted arrow in FIG. 13. This step also shifts the orientation of the sensor so the tracking system 130 outputs the orientation of the cutting surface of the instrument tip (instead of the sensor's orientation). When performing tip calibration the instrument is located so the cutting surface is at a known orientation, typically 0° azimuth, elevation and roll as shown in FIG. 14. This step can be achieved, by the tracking system 130, by adjusting the position and orientation offsets of the particular tracking system being used so the tracking system 130 outputs a specific 6DOF value, for example (10.00, 0.00, 0.00, 0.00, 0.00, 0.00), when the tip of the instrument 110 is located at a stored instrument tip location (for example, 10.00 inches in the +X direction and directly on the Y and Z axis as shown in FIG. 14).

The method 600 includes 640 sending, by the tracking system 130, the output of the location of the instrument 110, to a core system (e.g., the core system 150 in FIG. 1).

In some embodiments, if an instrument has two tips, the method 600 can include 650 sending, by the tracking system 130, a stored tip offset to the core system 150; and 660 determining, by the core system 150, an active tip based on the location of the instrument 110, the stored tip offset, and the location of the target 140. The stored tip offset can be a stored offset of the second tip relative to the first tip.

In some embodiments, to perform tip calibration, the tip of an instrument (or some spot on the cutting surface near the tip) can be held in a fixed position (x, y, z) while the orientation of the cutting surface is allowed to vary and then the instrument handle (including the sensor) is moved in a wide variety of positions around at least 2 axes, but the tip remains planted (fixed). The various positions of the sensor are recorded and this set of sensor positions (data set) is input to a computer program to determine the X, Y, and Z offsets from the magnetic center of the sensor to the tip (or spot on the cutting surface) that was held in the fixed position.

In some embodiments, target calibration can be eliminated by using assembly techniques such as pins and holes to provide the proper positioning and alignment of both the transmitter and a target. In some embodiments, a method of calibrating the location (position and orientation) of the target with respect to the transmitter is disclosed.

Figure 7:
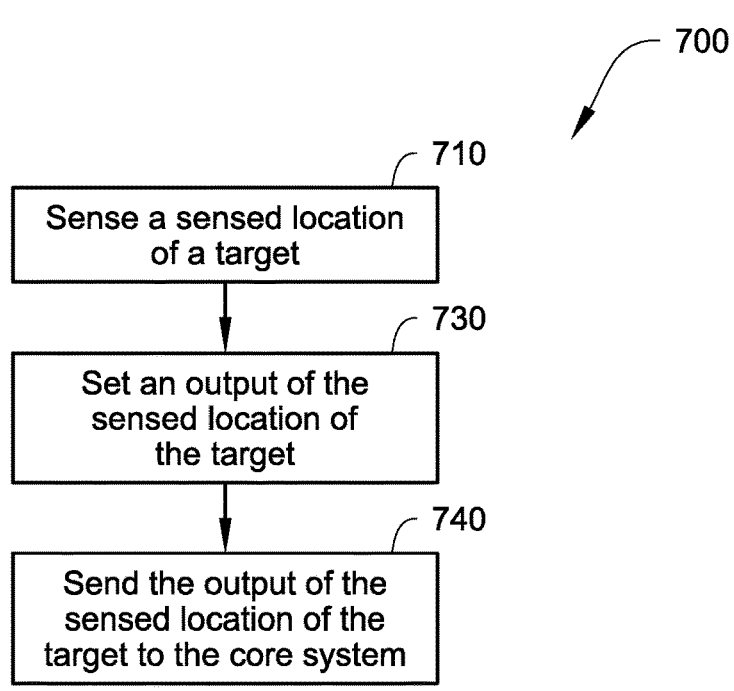
FIG. 7 is a flowchart of a method for calibrating a target, according to some embodiments.

FIG. 7 is a flowchart of a method 700 for calibrating a target (e.g. the target 140 in FIG. 1), according to some embodiments. The method 700 includes determining, by a core system (e.g., the core system 150 in FIG. 1), a location of the target 140 based on a stored target location. In some embodiments, the target 140 can be a typodont. The typodont can have a point, and the point can be located at a stored location. The typodont can have at least one tooth that has a plurality of facets. In some embodiments, the center point of the typodont can be located at a stored location, and the sensed/output location of the typodont can be the stored location.

In some embodiments, a target sensor (e.g., the target sensor 190 in FIG. 1) may be secured to the target 140. The method 700 includes 710 sensing, by a tracking system (e.g., the tracking system 130 in FIG. 1), a location of the target 140 using the target sensor 190 secured to the target 140.

At 730 the tracking system 130 sets an output of the sensed location of the target 140 to a value defined by the location of the target 140 and the stored target location. This step shifts the output of the location of the target 140, by the tracking system 130, to the location of the particular point instead of the target sensor (that is secured on the target) location. This step can be achieved, by the tracking system 130, by adjusting the angle align and offset factors and outputting a specific 6DOF value when the certain point of the target 140 is located at the stored target location.

At 740 the tracking system 130 sends the output of the sensed location of the target 140 to the core system 150.

In some embodiments, target calibration includes at least three calibration spots on the target in order to fully compensate for its location which includes both position (x, y, and z) and orientation (azimuth, elevation, and roll). In some embodiments, for improved accuracy, the three spots are separated on the three axes (x, y, and z) as shown in FIG. 15.

Figure 8:
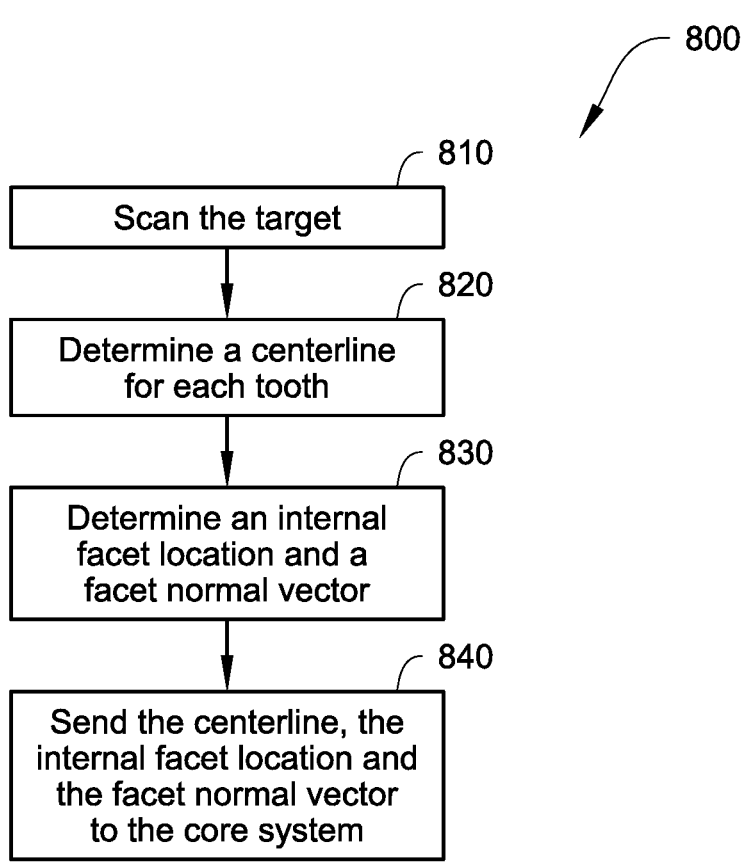
FIG. 8 is a flowchart of a method for scanning a target, according to some embodiments.

FIG. 8 is a flowchart of a method 800 for scanning a target (e.g., the target 140 in FIG. 1), according to some embodiments. In some embodiments, the target can have at least one tooth, the at least one tooth has a plurality of facets. The method 800 includes 810 scanning the target 140, by a scan system (e.g., the scan system 160 in FIG. 1) to get three-dimensional information of the target 140.

At 820 a centerline for each tooth is determined based upon the three-dimensional information.

In some embodiments, the target 140 can be scanned by the scan system 160 and each tooth in the target modeled in 3D so the internal/relative location (position and orientation) of each small triangular facet of the tooth is known. Once each tooth is modeled, a centerline for each tooth can be determined. The model information can be stored in the scan system 160.

At 830 an internal/relative facet location and a facet normal vector for each of the plurality of facets of each tooth is determined by the scan system 160, based upon the three-dimensional information. In some embodiments, based upon the three-dimensional information, the first facet of the first tooth can be determined, which can be assigned to a stored internal/relative location. The internal/relative location of other facets can be determined by calculating an offset relative to the location of the first facet of the first tooth. The internal/relative facet location, combined with the sensed/output location of the target, can define the actual location of the facet.

At 840 the centerline for each tooth, the internal facet location, and the facet normal vector for each of the plurality of facets of each tooth are sent to the core system (e.g., the core system 150 in FIG. 1).

Figure 9:
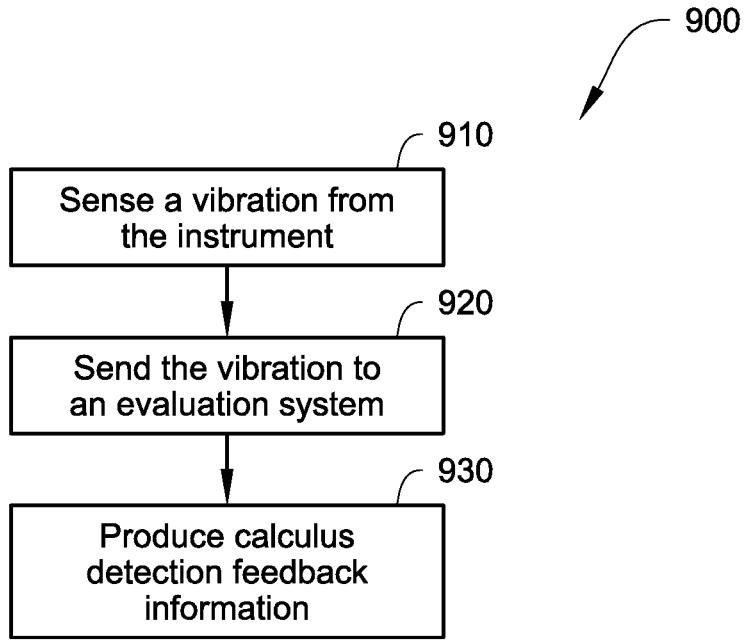
FIG. 9 is a flowchart of a method for detecting calculus, according to some embodiments.

FIG. 9 is a flowchart of a method 900 for detecting calculus, according to some embodiments. In some embodiments, a vibration sensor and/or force sensor (e.g., the vibration sensor and/or force sensor 180 in FIG. 1) can be secured to an instrument (e.g., the instrument 110 in FIG. 1), and a tracking system (e.g., the tracking system 130 in FIG. 1) can have a vibration sensor and/or force sensor (for example, an accelerometer) detector. In some embodiments, the target 140 can have at least one calculus.

In some embodiments, when the instrument 110 moves across some calculus, the instrument 110 can vibrate more than when the instrument is on a smooth, clean tooth surface.

In some embodiments, the vibration/force sensor 180 can determine a force (for example, pounds per square inch or ounces) applied in x, y, and z directions; detect when the instrument 110 (e.g., probe tip, cutting surface, etc.) is sliding along a smooth clean surface; and detect when the instrument gets caught along calculus (or cavity etc.). When the instrument 110 (e.g., probe tip, cutting surface, etc.) is obstructed, the vibration/force sensor 180 can indicate a spike in the force applied.

In some embodiments, the ability of the student to detect and locate calculus can be part of the proficiency score that the dental hygiene and periodontal hand instrumentation tutor 100 can provide to the student and/or instructor. The ability to detect and locate calculus can be very important when exploring invisible areas below the gum line.

In some embodiments, the system 100 can determine the type of calculus based on, for example, calculated adaptation angles of the instrument. The system 100 can also determine the location of calculus. In some embodiments, the calculus can be identified by attaching the calculus to the typodont and then scanning the typodont with the calculus on.

At 910 the tracking system 130 senses a vibration from the instrument 110 when the instrument 110 is contacted with the target 140. At 920 a notification of the vibration is sent by the tracking system 130, through the core system (e.g., the core system 150 in FIG. 1), to an evaluation system (e.g., the evaluation system 170 in FIG. 1). At 930 calculus detection feedback information (such as, but not limited to, a difference between the vibration and at least one stored vibration) is produced by the evaluation system 170. The feedback information can help eliminate subjective, inconsistent, and/or imprecise results obtained by a human observer; can help or tutor any hygiene student, from beginner to advanced, to improve their accuracy, consistency and speed when learning to use a wide variety of dental hygiene and periodontal hand instrumentation; and can ensure the dental instrument is used correctly to maximize the tools effectiveness while minimizing the chance of harm to a live patient.

In some embodiments, the force or vibration sensed at 910 can include a hand to instrument pressure and an instrument to tooth pressure. The hand to instrument pressure can be sensed by a sensor (for example, an accelerometer) installed on the instrument. The hand to instrument pressure can be used to detect how hard the student is gripping the instrument. If a student holds on the instrument too tightly, it may reduce tactile sense (i.e., the ability to find calculus and follow root anatomy). The instrument to tooth pressure can be sensed by a sensor (for example, an accelerometer) installed on a target (for example, a tooth).

Figure 10A:
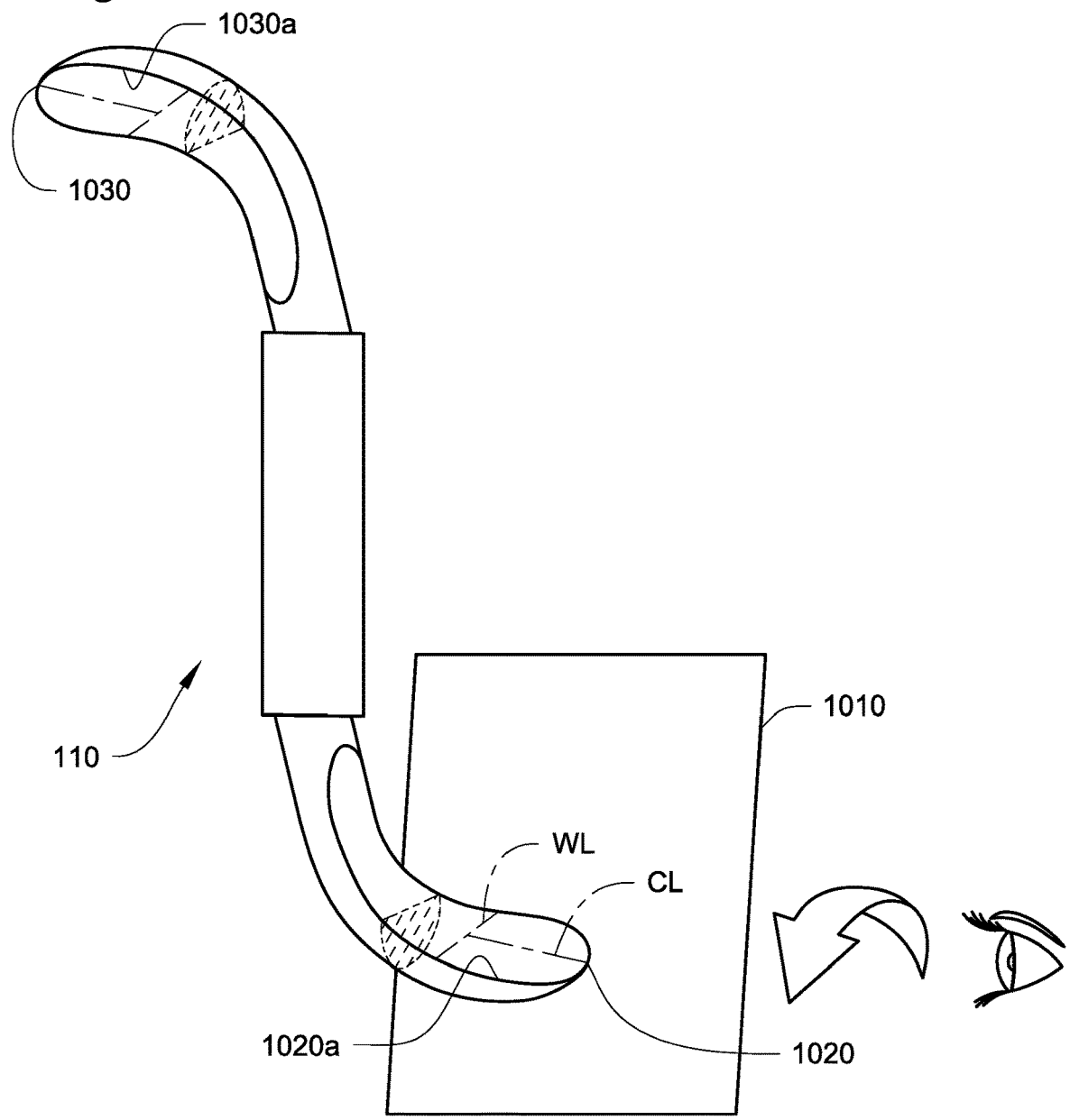
FIG. 10A and FIG. 10B are end/tip views of an angulation angle, according to some embodiments.
Figure 10B:
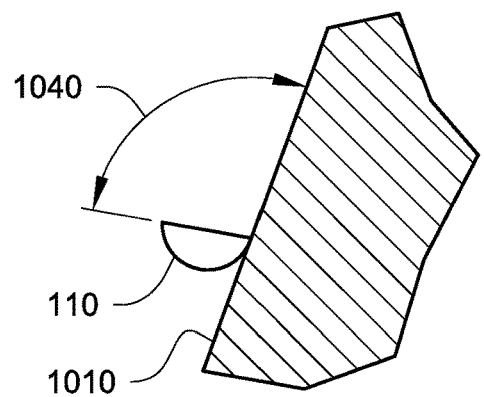
Figure 10C:
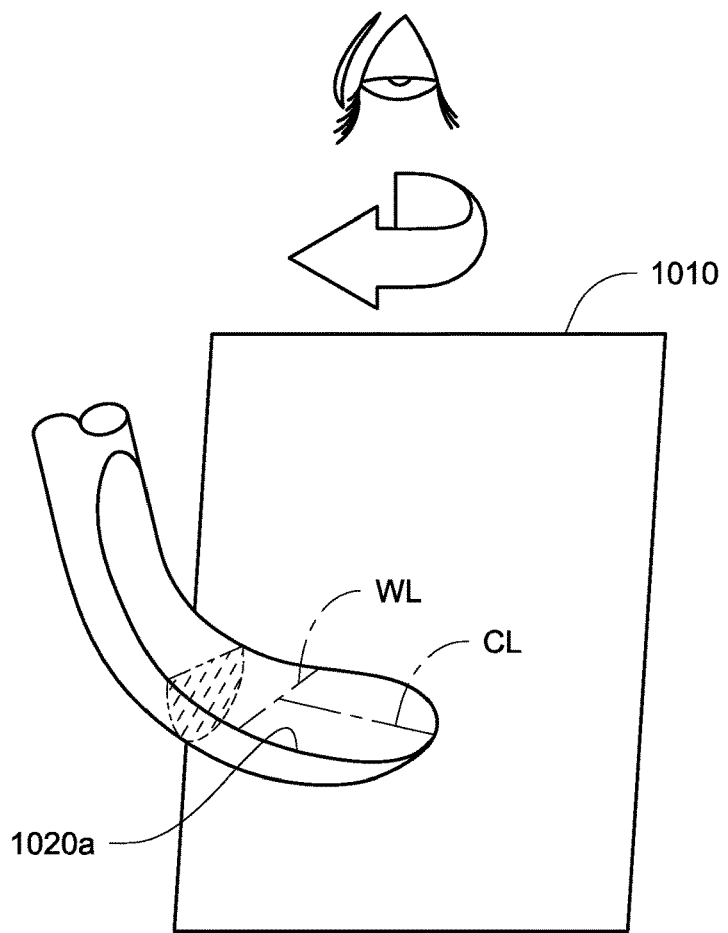
FIG. 10C and FIG. 10D are top views of an adaptation angle, according to some embodiments.
Figure 10D:
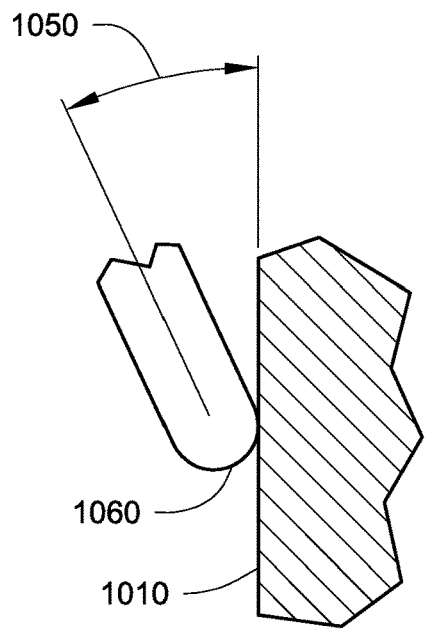
Figure 16:
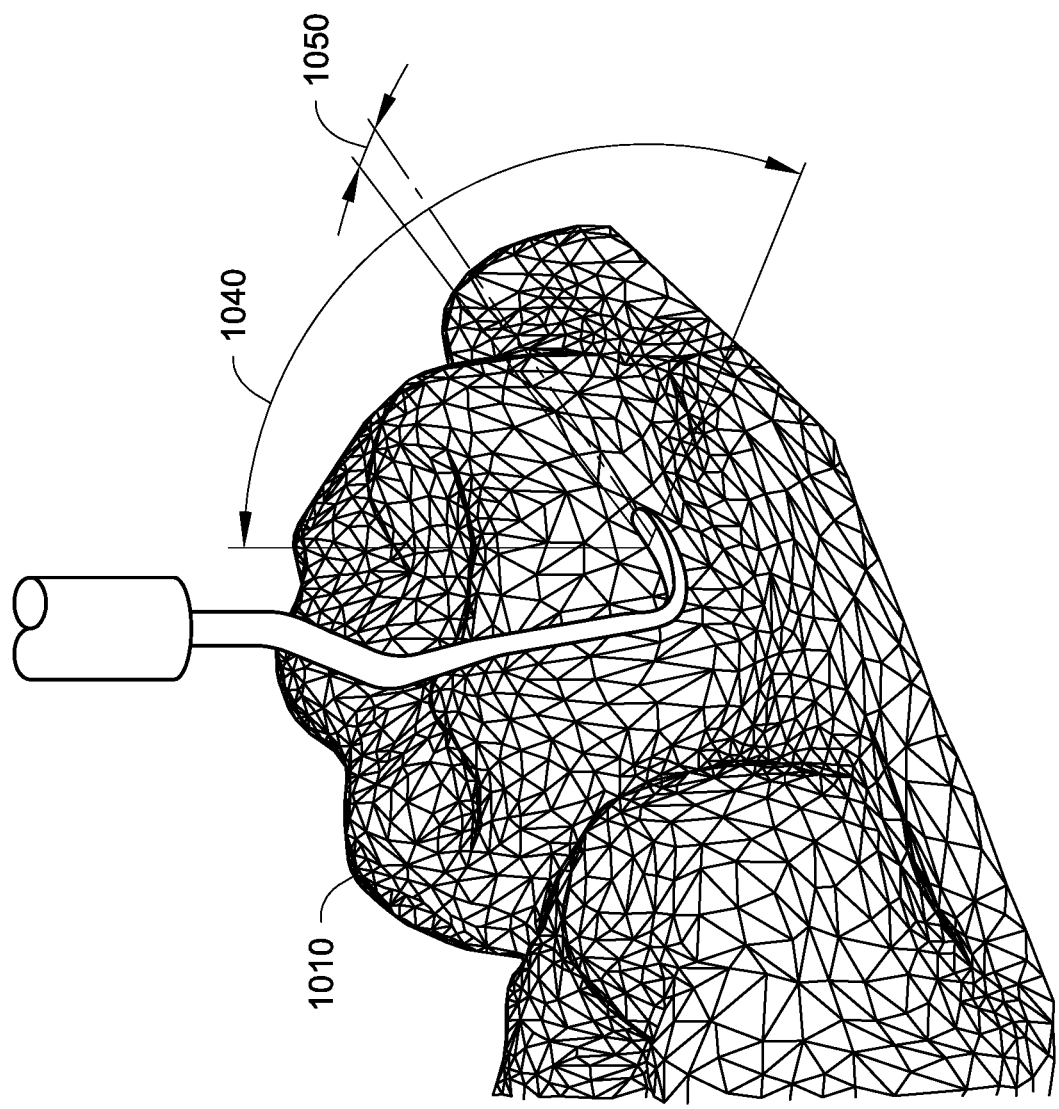
FIG. 16 is a combined view showing both the angulation angle and the adaptation angle between the instrument cutting surface and the tooth surface, according to some embodiments.

FIG. 10A and FIG. 10B are end/tip views of an angulation angle, according to some embodiments. FIG. 10C and FIG. 10D are top views of an adaptation angle, according to some embodiments. FIG. 16 is a combined view showing both the angulation angle and the adaptation angle between the instrument cutting surface and the tooth surface, according to some embodiments.

FIGS. 10A, FIG. 10B, FIG. 10C, and FIG. 10D show a tooth facet 1010. FIG. 10A also shows an instrument 110. In some embodiments, the instrument 110 can have a first tip 1020 and a second tip 1030. The first tip 1020 can have a cutting surface 1020a and the second tip 1030 can have a cutting surface 1030a.

FIG. 10A shows that the cutting surfaces 1020a, 1030a can have respective center line (CL) and width line (WL). FIG. 11B also shows that the CL and WL define the cutting surface and their respective normal unit vector T. In some embodiments, the tracking system can determine the CL and WL of the cutting surface along with their corresponding directions when sensing the location of the instrument.

FIG. 10B shows an angulation angle 1040. FIG. 10D shows an adaptation angle 1050 and an instrument tip 1060. The instrument tip 1060 can be the first tip 1020 or the second tip 1030 of the instrument 110.

In some embodiments, the dental hygiene and periodontal hand instrumentation tutor 100 includes a method to monitor two instrument tips with only one sensor. To a casual observer it may seem like an instrument handle could be located in many different locations while still having the instrument tip in the correct position to generate the correct angulation and adaptation angles. However, that understanding is not correct. In some embodiments, an appropriate way to have the instrument tip in the right position and orientation is to also have the center of the handle in the right position and orientation. In some embodiments, a single sensor can be mounted near the center of the handle and measure the desired angles at both ends of the instrument (for example, a double headed instrument with only one sensor).

In some embodiments, for improved accuracy, the dental hygiene and periodontal hand instrumentation tutor 100 may use two sensors per instrument with each sensor mounted close to one of the tips. The system (for example, the core system 150) can use the output from both sensors regardless of which tip is next to a target tooth. The sensor closest to the tip being used (i.e., next to a target facet) can have higher accuracy because of smaller offsets (the distance from magnetic center of the sensor to a particular tip). Therefore, the location data (position and orientation) from that sensor can be given more weight than the other sensor. However, the other sensor location will still be used (at the same time) to help eliminate noise from nearby metal or interference signals. Through various filtering techniques, using two sensors at the same time can improve the overall accuracy of the position and orientation of the tip being used (i.e., the one next to the target facet).

In some embodiments, the dental hygiene and periodontal hand instrumentation tutor 100 can record the angulation and adaptation and centerline angles from start to finish as a user completes a cleaning stroke. The recorded data can be saved and played back to the student and/or instructor along with 3D graphics to illustrate where in the stroke one or more angles were incorrect and why they were incorrect.

Figure 11A:
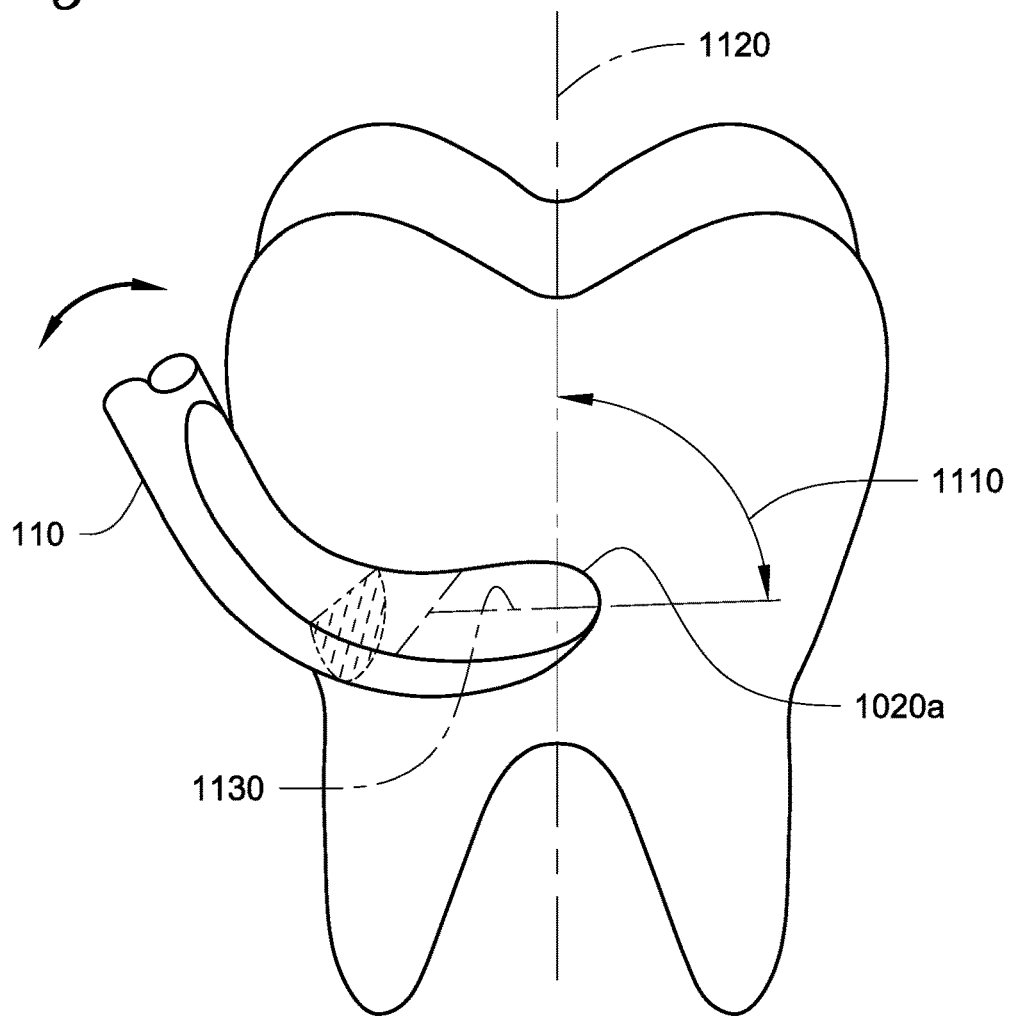
FIG. 11A is a side view of a centerline angle, according to some embodiments.
Figure 11B:
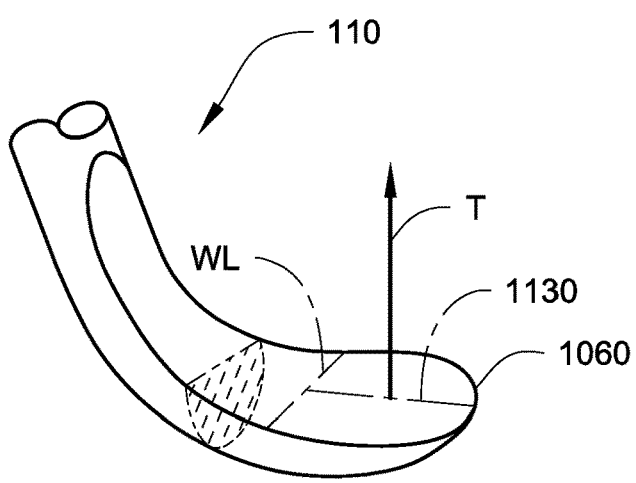
FIG. 11B shows the normal unit vector of an instrument's cutting surface, according to some embodiments.
Figure 11C:
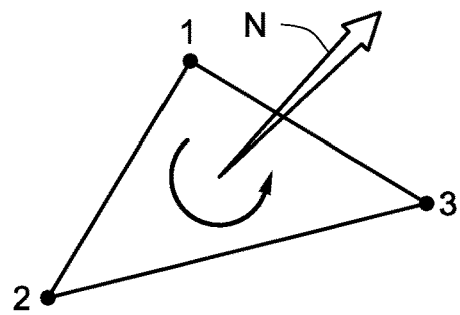
FIG. 11C shows the normal unit vector of one facet of a tooth surface, according to some embodiments.

FIG. 11A is a side view of a centerline angle 1110, according to some embodiments. The centerline angle 1110 can be defined by the centerline 1120 of the tooth and CL 1130 of the cutting surface. FIG. 11B shows the normal unit vector T of a cutting surface of the instrument 110, according to some embodiments. FIG. 11B also shows an instrument tip 1060. The instrument tip 1060 can be the first tip 1020 or the second tip 1030 of an instrument. FIG. 11C shows the normal unit vector N of one facet of a tooth surface, according to some embodiments.

Figure 12:
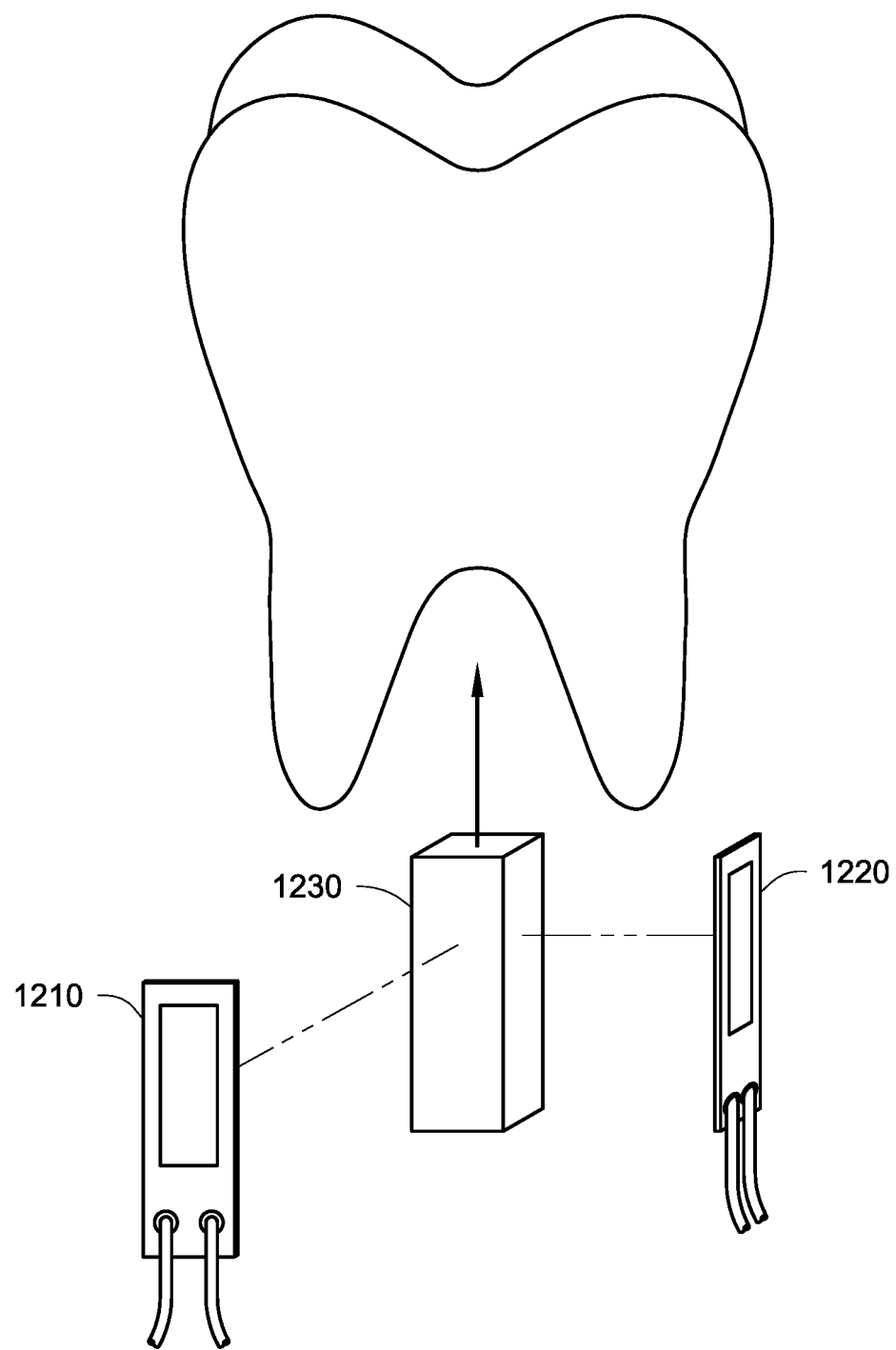
FIG. 12 shows force sensors secured to a root area of a tooth, according to some embodiments.

FIG. 12 shows force sensors secured to a root area of a tooth, according to some embodiments. In some embodiments, one or more force sensors (such as, but not limited to, load cells, etc.) can be secured to a target 140 to measure the force applied in one or more directions. In some embodiments, three force sensors can be secured, for example, to the root area of one or more teeth of the target 140 (e.g., a typodont, etc.) to measure force in x, y, and z directions on a surface/facet of a tooth where a tip of a dental instrument is used. In some embodiments, user feedback information can be provided by an evaluation system 170 to ensure the proper amount of instrument tip force is being applied so the cutting surface of the instrument tip will remove calculus but will not harm the tooth surface/facet. The dental hygiene and periodontal hand instrumentation tutor 100 can teach students how hard to press the tip of the instrument 110 on the tooth surface/facet so the students can efficiently remove calculus without harming the tooth. It is to be appreciated that most beginners press far too soft or hard.

In some embodiments, the force sensors can be secured to the instrument 110 instead of the target 140 so that the force sensors could measure the instrument tip force on any target.

In FIG. 12, the arrow and the dashed lines indicate the directions, including the directions in which force sensor 1210 and force sensor 1220 are secured to load sensor beam 1230, and the direction in which the load sensor beam 1230 is secured to the tooth. In some embodiments, a bottom of the load sensor beam 1230 can be fixed to a typodont but a top of the load sensor beam 1230 (with tooth attached) can be floating and free to move (for example, microscopically) allowing the force sensors 1210 and 1220 to measure side or lateral forces. The embodiment as shown in FIG. 12 can, for example, measure how hard the student is pressing into the tooth surface on any side of the tooth.

Figure 13A:
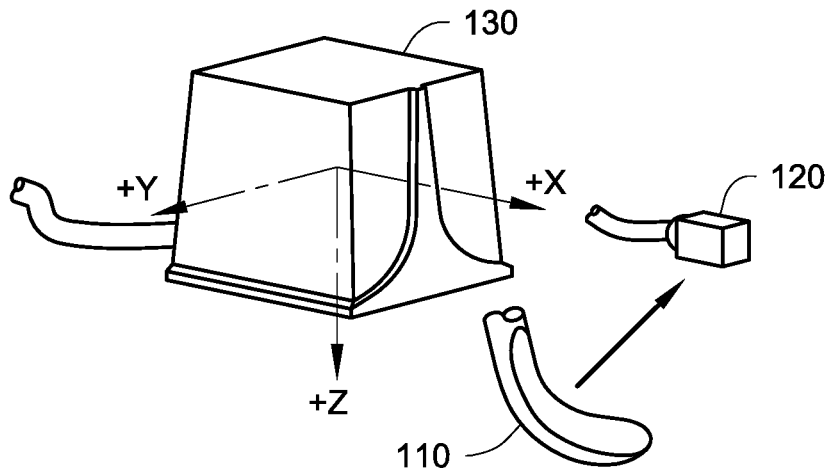
FIGS. 13A-13D show a coordinate system for a transmitter and a sensor, according to some embodiments.
Figure 13B:
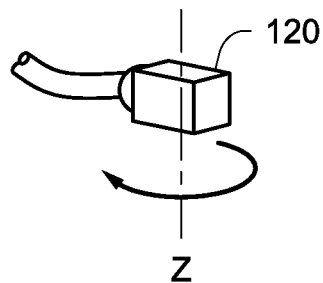
Figure 13C:
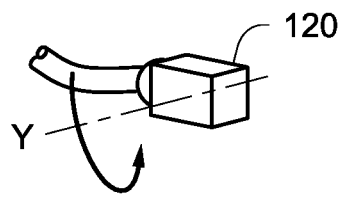
Figure 13D:
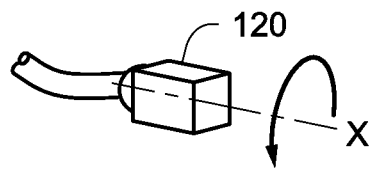
Figure 14:
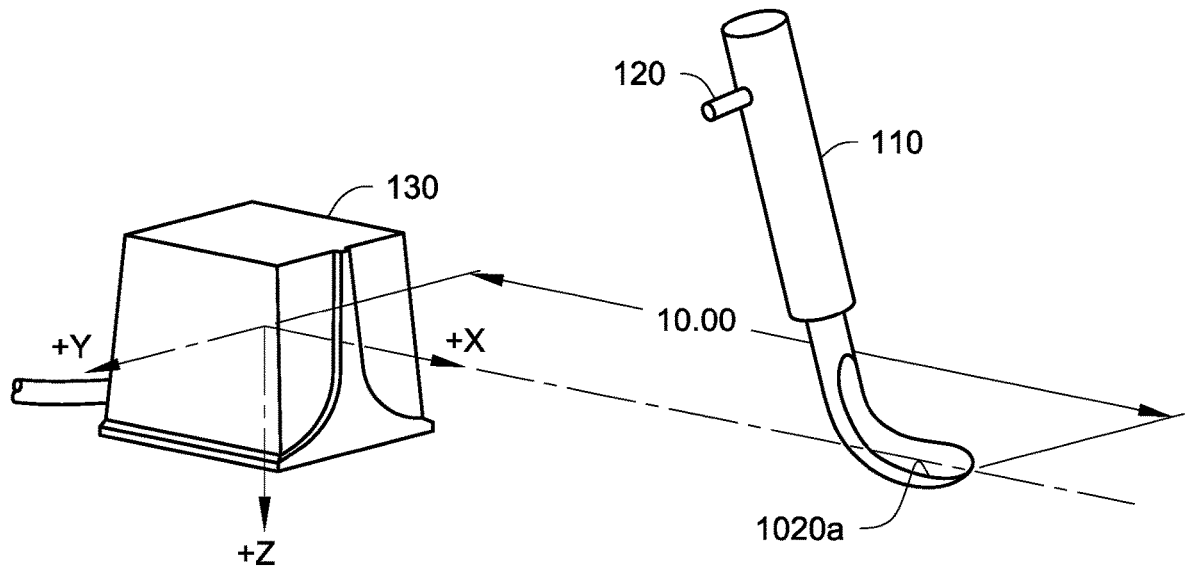
FIG. 14 shows a tip position of and a cutting surface orientation of an instrument, according to some embodiments.

FIG. 13A shows a coordinate system for a transmitter 130 and the sensor 120, according to some embodiments. The arrows +X, +Y, and +Z show positive direction for position data. Position (0, 0, 0) is the center position of the transmitter 130. Arrows in FIGS. 13B-13D show positive direction for azimuth (FIG. 13B, rotation around Z axis), elevation (FIG. 13C, rotation around Y axis), and roll (FIG. 13D, rotation around X axis).

FIG. 14 shows after tip calibration, a tip position of (10.00, 0.00, 0.00) and a cutting surface orientation of (0.0, 0.0, 0.0), according to some embodiments. Therefore, the location of the tip of the instrument is (10.00, 0.00, 0.00, 0.0, 0.0, 0.0).

FIG. 15 shows three calibration spots on a target for target calibration, according to some embodiments. In some embodiments, target calibration requires at least three calibration spots on the target in order to compensate for both position (x, y, and z) and orientation (azimuth, elevation, and roll) of the target with respect to the transmitter.

FIG. 16 is a combined view showing both the angulation angle and the adaptation angle between the instrument cutting surface and the tooth surface, according to some embodiments.

Aspects:

It is to be appreciated that any of aspects 1-8 can be combined with any one of aspects 9-15 and/or 16-30. It is further to be appreciated that any one of aspects 9-15 can be combined with any one of aspects 16-30.

Aspect 1. A method, comprising:
obtaining from a tracking system, by a core system, a location of an instrument, the location of the instrument having an orientation and a position;
obtaining from the tracking system, by the core system, a location of a target, the target having a surface, the location of the target having an orientation and a position;
calculating an angulation angle, by the core system, based upon the orientation of the instrument and the orientation of the target surface;
sending the angulation angle, by the core system, to an evaluation system; and
producing angulation angle feedback information by the evaluation system.

Aspect 2. The method according to aspect 1, further comprising:
calculating an adaptation angle, by the core system, based upon the orientation of the instrument and the orientation of the target surface;
sending the adaptation angle, by the core system, to the evaluation system; and
producing adaptation angle feedback information by the evaluation system.

Aspect 3. The method according to any one of aspects 1-2, further comprising:
determining a tooth-centerline, by the core system, based upon the location of the target;
determining a surface-centerline, by the core system, based upon the location of the instrument;
calculating a centerline angle, by the core system, based upon the surface-centerline and the tooth-centerline;
sending the centerline angle, by the core system, to the evaluation system; and
producing centerline angle feedback information, by the evaluation system.

Aspect 4. The method according to any one of aspects 1-3, further comprising:
determining at least one tooth-facet plane or vector, by the core system, based upon the location of the instrument;
determining a motion path of the instrument, by the core system, based on the location of the instrument and the at least one tooth-facet plane or vector;
sending the location of the instrument and the motion path of the instrument, by the core system, to the evaluation system; and
producing instrument location feedback and instrument motion path feedback information by the evaluation system.

Aspect 5. The method according to any one of aspects 1-4, wherein the evaluation system displays one or more of the angulation angle, the at least one stored angulation angle, the adaptation angle, the at least one stored adaptation angle, the centerline angle, the at least one stored centerline angle, the location of the instrument, the at least one stored instrument location, the motion path of the instrument, and/or the at least one stored instrument motion path.

Aspect 6. The method according to any one of aspects 1-5, wherein the evaluation system displays user evaluation information, the user evaluation information being in a digital, analog, graphical, avatar, alarm, and/or voice format.

Aspect 7. The method according to any one of aspects 1-6, wherein the evaluation system displays a dental hygiene proficiency score and/or a dental hygiene scaling score.

Aspect 8. The method according to any one of aspects 1-7, wherein the tracking system is one of a magnetic tracking system, a visible optical tracking system, an invisible optical tracking system, an ultrasonic tracking system, a radar tracking system, an accelerometer tracking system, a gyroscopic tracking system, an inclinometer tracking system, an inertial measurement unit tracking system, and/or a mechanical linkage tracking system.

Aspect 9. A method, comprising:
sensing, by a tracking system, a location of a target using a target sensor associated with the target;
setting, by the tracking system, an output of the location of the target to a value defined by the location of the target and the stored target location; and
sending, by the tracking system, the output of the location of the target to the core system.

Aspect 10. The method according to aspect 9, wherein the target sensor is secured to the target.

Aspect 11. The method according to any one of aspects 9-10, further comprising:
determining, by a core system, a location of the target from a stored target location.

Aspect 12. The method according to aspect 11, further comprising:
determining, by the core system, an active tip based on a location of an instrument, a stored tip offset, and the output of the location of the target.

Aspect 13. The method according to any one of aspects 11-12, wherein the target has at least one tooth and the at least one tooth has a plurality of facets, further comprising:
scanning the target, by a scan system, to get three-dimensional information of the target;
determining a centerline for each of the at least one tooth based upon the three-dimensional information;
determining an internal facet location and a facet normal unit vector for each of the plurality of facets of each of the at least one tooth, by the scan system, based upon the three-dimensional information; and
sending the centerline for each of the at least one tooth, the internal facet location and the facet normal unit vector for each of the plurality of facets of each of the at least one tooth to the core system.

Aspect 14. The method according to any one of aspects 12-13, wherein an accelerometer is secured to the instrument, the tracking system having an accelerometer detector, further comprising:
installing at least one piece of calculus on the target;
sensing, by the tracking system, a vibration from the instrument being contacted with the target;
sending the vibration, by the tracking system through the core system, to an evaluation system; and
producing calculus detection feedback information by the evaluation system.

Aspect 15. The method according to any one of aspects 12-14, wherein a force sensor is secured to the target, the tracking system having a force sensor detector, further comprising:
sensing, by the tracking system, a force from the target being contacted with the instrument;
sending the force, by the tracking system through the core system, to an evaluation system; and
producing force detection feedback information by the evaluation system.

Aspect 16. A dental hygiene and periodontal hand instrumentation tutor comprising:
a dental hygiene and periodontal hand instrumentation;

an instrument sensor for determining a position and orientation of the instrument;

a tracking system in communication with the instrument sensor;

a core system in communication with the tracking system; and an evaluation system in communication with the core system.

Aspect 17. The dental hygiene and periodontal hand instrumentation tutor according to aspect 16, wherein the instrument sensor is secured to the instrument.

Aspect 18. The dental hygiene and periodontal hand instrumentation tutor according to any one of aspects 16-17, wherein the instrument sensor is an optical sensor, and the instrument includes an optical target for the optical sensor.

Aspect 19. The dental hygiene and periodontal hand instrumentation tutor according to any one of aspects 16-18, further comprising:

a target in communication with the tracking system, wherein the target has at least one tooth, the at least one tooth has a plurality of facets.

Aspect 20. The dental hygiene and periodontal hand instrumentation tutor according to any one of aspects 16-19, wherein the instrument has a handle and at least one tip.

Aspect 21. The dental hygiene and periodontal hand instrumentation tutor according to any one of aspects 16-20, wherein the at least one tip has a cutting surface.

Aspect 22. The dental hygiene and periodontal hand instrumentation tutor according to any one of aspects 16-21, wherein the tracking system is in communication with the instrument sensor wirelessly or through wire;

the core system is in communication with the tracking system wirelessly or through wire; and the evaluation system is in communication with the core system wirelessly or through wire.

Aspect 23. The dental hygiene and periodontal hand instrumentation tutor according to any one of aspects 16-22, further comprising:

an accelerometer secured to the instrument.

Aspect 24. The dental hygiene and periodontal hand instrumentation tutor according to any one of aspects 19-23, further comprising:

a target sensor secured to the target.

Aspect 25. The dental hygiene and periodontal hand instrumentation tutor according to any one of aspects 23-24, wherein the accelerometer is in communication with the tracking system wirelessly or through wire.

Aspect 26. The dental hygiene and periodontal hand instrumentation tutor according to any one of aspects 24-25, wherein the target sensor is in communication with the tracking system wirelessly or through wire.

Aspect 27. The dental hygiene and periodontal hand instrumentation tutor according to any one of aspects 16-26, wherein the evaluation system displays one or more of the angulation angle, the at least one stored angulation angle, the adaptation angle, the at least one stored adaptation angle, the centerline angle, the at least one stored centerline angle, the location of the instrument, the at least one stored instrument location, the motion path of the instrument, and/or the at least one stored instrument motion path.

Aspect 28. The dental hygiene and periodontal hand instrumentation tutor according to any one of aspects 16-27, wherein the evaluation system displays user evaluation information, the user evaluation information being in a digital, analog, graphical, avatar, alarm, and/or voice format.

Aspect 29. The dental hygiene and periodontal hand instrumentation tutor according to any one of aspects 16-28, wherein the evaluation system displays a dental hygiene proficiency score and/or a dental hygiene scaling score.

Aspect 30. The dental hygiene and periodontal hand instrumentation tutor according to any one of aspects 16-29, wherein the tracking system is one of a magnetic tracking system, a visible optical tracking system, an invisible optical tracking system, an ultrasonic tracking system, a radar tracking system, an accelerometer tracking system, a gyroscopic tracking system, an inclinometer tracking system, an inertial measurement unit tracking system, and/or a mechanical linkage tracking system.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, indicate the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts, without departing from the scope of the present disclosure. The word "embodiment" as used within this specification may, but does not necessarily, refer to the same embodiment. This specification and the embodiments described are examples only. Other and further embodiments may be devised without departing from the basic scope thereof, with the true scope and spirit of the disclosure being indicated by the aspects that follow.

What is claimed is:

1. A dental hygiene and periodontal hand instrumentation tutor, comprising:

a dental hygiene and periodontal hand instrument;

an instrument sensor for determining a position and an orientation of the instrument;

a target in communication with a tracking system, the target comprising a target surface and a target sensor for determining a position and an orientation of the target surface;

the tracking system in communication with the instrument sensor, the tracking system being configured to determine the position and the orientation of the instrument and the position and an orientation of the target surface;

a core system in communication with the tracking system, the core system being configured to calculate an angulation angle, an adaptation angle based upon the orientation of the instrument and the orientation of the target surface, and a motion path of the instrument, wherein the instrument comprises a trigger configured to indicate a beginning and an end of the motion path of the instrument when triggered by a user;

and an evaluation system in communication with the core system, the evaluation system being configured to produce at least one of angulation angle feedback information, adaptation angle feedback information, instrument location feedback, or instrument motion path feedback information, and sending correction feedback to the user showing how to make corrections to at least one of the motion path, the angulation angle, or the adaption angle of the instrument, and a dental hygiene proficiency score and/or a dental hygiene scaling score based on parameters of how well the angulation angle and the adaptation angles are maintained throughout the motion path of the instrument and/or how well the motion path of the instrument tracks an ideal motion path, based on the respective at least one of the angulation angle feedback information, the adaptation angle feedback information, the instrument location feedback, or the instrument motion path feedback information, wherein the correction feedback includes at least one of sounds or vibration.

2. The dental hygiene and periodontal hand instrumentation tutor according to claim 1, wherein the instrument sensor is secured to the instrument.

3. The dental hygiene and periodontal hand instrumentation tutor according to claim 1, wherein the instrument sensor is an optical sensor, and the instrument includes an optical target for the optical sensor.

4. The dental hygiene and periodontal hand instrumentation tutor according to claim 1, wherein the target has at least one tooth, the at least one tooth has a plurality of facets.

5. The dental hygiene and periodontal hand instrumentation tutor according to claim 1, wherein the core system is further configured to determine at least one tooth-facet plane or based upon the location of the instrument; determine the motion path of the instrument based on the position and the orientation of the instrument and the at least one tooth-facet plane or vector; and send the position and the orientation of the instrument and the motion path of the instrument to the evaluation system.

6. The dental hygiene and periodontal hand instrumentation tutor according to claim 1, wherein the core system is further configured to determine an active tip based on the position and the orientation of the instrument and the position and the orientation of the target surface.

7. The dental hygiene and periodontal hand instrumentation tutor according to claim 1, wherein an accelerometer is secured to the instrument and the tracking system includes an accelerometer detector, wherein the tracking system is configured to sense a vibration from the instrument being contacted with the target and send a notification of the vibration through the core system to the evaluation system, and the evaluation system is configured to produce calculus detection feedback information.

8. The dental hygiene and periodontal hand instrumentation tutor according to claim 1, wherein a force sensor is secured to the target and the tracking system includes a force sensor detector, wherein the tracking system is configured to sense a pressure from the target being contacted with the instrument and send indication of the pressure through the core system to the evaluation system; and the evaluation system is configured to produce pressure detection feedback information.

* * * * *